United States Patent
Yang et al.

[19]

[11] Patent Number: 6,167,290

[45] Date of Patent: Dec. 26, 2000

[54] METHOD AND APPARATUS OF NON-INVASIVE MEASUREMENT OF HUMAN/ANIMAL BLOOD GLUCOSE AND OTHER METABOLITES

[75] Inventors: Wei Yang, Fremont, Calif.; Shu Zhang, Waterloo, Canada

[73] Assignee: Bayspec, Inc., Fremont, Calif.

[21] Appl. No.: 09/244,330

[22] Filed: Feb. 3, 1999

[51] Int. Cl.$^7$ .................................................. A61B 5/00
[52] U.S. Cl. ........................................ 600/322; 600/316
[58] Field of Search .................................. 600/316, 322, 600/334, 335, 365

[56] References Cited

U.S. PATENT DOCUMENTS

| | | | |
|---|---|---|---|
| 5,109,849 | 5/1992 | Goodman et al. | 600/483 |
| 5,827,181 | 10/1998 | Dias et al. | 600/322 |

*Primary Examiner*—Eric F. Winakur
*Attorney, Agent, or Firm*—Oppenheimer Wolff & Donnelly LLP

[57] ABSTRACT

A method and apparatus for non-invasively measuring animal/human blood glucose and other metabolites including an excitation laser source, a negative pressure based sampling port which interfaces to a human or other animal tissue sample in vivo, a Raman spectrometer, and data analysis and display devices. The device can be made in a compact size and may be portable, and it can be used in homes, offices or clinics. A negative atmospheric sampling port is made of a vacuum chamber that is connected with an electrically or manually driven vacuum pump which creates a negative air pressure inside the vacuum chamber. Under the negative air pressure, a substantial amount of blood is "sucked" into a small area of the human finger so that measurement of an enhanced Raman signal can be made.

20 Claims, 5 Drawing Sheets

RAMAN SPECTROMETER

METHOD AND APPARATUS OF NON-INVASIVE MEASUREMENT OF HUMAN/ANIMAL BLOOD GLUCOSE AND OTHER METABOLITES

FIELD OF THE INVENTION

This invention generally relates to methods and apparatus for non-invasive measurement of human/animal blood glucose level, and in particular, for monitoring blood glucose levels for diabetes. The apparatus is suitable for home or clinical use as a portable blood glucose monitor/analyzer and does not require that blood samples be drawn.

BACKGROUND OF THE INVENTION

There are approximately 100 millions people in the world that are diabetic, and many millions of them are in the U.S. Knowledge of blood glucose composition is of crucial importance for treating diabetes. Moreover, information on variations of blood glucose level during an extended period of time is very important in a diabetic patient's daily life since poor glucose control over time can lead to severe complications, including blindness, kidney failure, heart failure, limb pain, poor circulation and subsequent amputation. Currently, diabetic patients must use often painful and cumbersome tests requiring them to repeatedly lance their finger and draw blood. After separate setup steps, including drawing blood with a lancet, the blood is then placed on a diagnostic test strip composed of chemicals sensitive the glucose in the blood sample, and the strip is read by a meter. In order to properly monitor and control the glucose level, an adult diabetic must normally take blood measurements 4–7 times a day, while children and elderly etc. may need to take blood samples up to 10 times daily. The tests are painful and costly, and the blood disposal and contamination are also potential problems.

For a number of years, attempts have been made to determine blood glucose level non-invasively (or in vivo) using optical radiation, or in general, lightwave technologies. For example, techniques including visible, near-infrared (IR) spectroscopy, mid-infrared (MIR) spectroscopy, infrared (IR) spectroscopy, polarization changes, scatter changes, photoacoustic spectroscopy, Raman scattering through tissue or human eyes, etc. To date, none of these approaches have been feasible, furthermore, none of the other types of non-invasive technology has been feasible either. As a result, there is a need for a personal or clinical non-invasive glucose monitoring system for monitoring blood glucose level without pain and requiring the drawing of a blood sample.

Visible and near-infrared (NR) spectroscopic techniques have been used to measure blood glucose level non-invasively. These techniques utilize optical radiation in the wavelength range of 600 nm–2500 nm, to measure basically the absorption of glucose in blood by either transmitting the optical radiation through, or reflecting from, a portion of human tissue, such as a finger or ear lobe. The absorption spectra obtained from the measurements are then analyzed to derive the glucose level. These techniques cannot satisfy the need to monitor glucose level non-invasively due to the many intrinsic drawbacks of NIR spectroscopy. It is known that NR wavelengths do not measure fundamental vibrational transition modes of molecules; only longer wavelengths, i.e., mid-infrared (MIR) and infrared (IR) wavelengths can measure the fundamental vibrational transitions which produce spectral "finger-print" effects. For example, IR spectroscopic techniques generate specific, sharp spectral peaks that directly correlate to specific molecules, and the height of the spectral peaks are directly proportional to the concentration of the molecules. However, NIR spectra contain many harmonics of overtones as well as a combination of various fundamental vibration transitions. There is small possibility of a specific spectral peak that directly correlates to a specific molecule, i.e., the enegetics associated with overtones and combination of absorption results in absorption bands that are broad and featureless with low absorptivities. Moreover, glucose produces one of the weakest NIR absorption signals per concentration unit of the body's major components. For example, water has very strong absorption signals in the NIR region, especially in the 900–2500 nm wavelength regions. Since a large portion of human tissue is water, it is very difficult, if not impossible, to make non-invasive glucose measurement using NIR techniques without water interference. Furthermore, NIR techniques are vulnerable to interference from environmental variations, such as temperature, humidity changes; thus, it is hardly acceptable for home or clinical use. Despite the fact that many attempt have been made over the years, NIR techniques are still unable to measure blood glucose non-invasively. Due to the many aforementioned drawbacks of the NIR techniques, none of the devices based on the techniques have been able to measure the blood glucose level accurately and repeatedly.

In other prior art technologies, mid-infrared (MIR) and Infrared (IR) techniques are used in a similar fashion as the aforementioned NIR techniques. For example, these techniques utilize optical radiation in the wavelength range of 3000 nm–10,000 nm to measure basically the absorption of glucose in blood in a portion of human tissue, such as a finger or ear lobe or even a lip. These technologies in principle correct the major drawbacks that are associated with NIR technology, in that the MIR techniques generate spectra containing fundamental vibrational transitions. The water interference to these longer wavelengths, however, is orders of magnitude stronger than that of the NIR region. It is evident in many publications and acknowledged in prior art that the absorption of human skin is substantially higher for longer wavelengths, and absorption is nonlinear. For example, the strong absorption of human tissue is acknowledged in U.S. Pat. No. 5,553,616. Due to the strong interference from absorption of the skin (which is mainly water), MIR or IR optical radiation has a hard time penetrating to a reasonable depth of human tissue, thereby rendering infrared spectroscopic measurement useless in term of non-invasively monitoring blood glucose level.

In still another prior art technology, laser Raman spectroscopy is used to obtain glucose to concentration. In this process, a laser beam is focused into a human subject's eye where it interacts with the ocular aqueous humor and generates Raman scattering, which is collected and analyzed by a Raman spectrometer to obtain a Raman spectrum of the aqueous humor. The prior art claims that glucose concentration in the ocular aqueous humor can be derived from the Raman spectrum, then the blood glucose level can be inferred. Such process is described in U.S. Pat. No. 5,243,983. This technology in theory corrects some of the major drawbacks associated with the aforementioned NIR, MIR and IR technologies. For example, Raman spectroscopic techniques not only generate spectra with spectrally differentiable features for different constituents in a sample, but also employ visible (400–700 nm) and short NIR (800–1100 nm) wavelengths which are not absorbed by water as strongly as is the case with MIR and IR wavelengths. Despite of the fact that the device in the aforementioned U.S.

Pat. No. 5,243,983 uses an optically more "clear window", i.e., the human eye, rather than human tissue, it is not an ideal device, and it may not even be a safe device. It is a known fact that the human eyes are very vulnerable to bright light illumination, especially laser radiation. The permissible level of laser exposure to the human eye is so low that it may not even be enough to produce the Raman signal required to derive the glucose concentration. Furthermore, eye safety is a major concern for such a device designed for daily home or clinic use by an average diabetic patient.

Raman spectroscopy is also used in other prior art devices to measure glucose non-invasively by focusing or delivering laser radiation directly to human tissues to measure concentrations of blood glucose or other analytes such as blood gases in vivo. The laser beam interacts with a portion of human skin or an index finger and generates Raman scattering, which is collected and analyzed by a Raman spectrometer to obtain a Raman spectrum. Despite the fact that these prior art methods using a laser to directly interact with human tissues and thus avoid the dangerous problems of laser safety associated with focusing a laser into the human eye, they still have major drawbacks and are thus still not successful.

The major drawback of the above-described prior art is the difficulty that the very weak Raman signal has in migrating through human tissue, which is mostly inhomogeneous turbid media. It is well known, as discussed in many publications, that Raman spectroscopy is based on inelastic light scattering in which scattered photons exchange energy with the sample. Raman scattering is a weak effect with only about 1 photon in $10^6$–$10^8$ incident on the sample exhibiting a Raman shift. One way to obtain more Raman signal is, to simply increase the excitation laser power to a higher level. This increasing of laser power, however, runs the risk of burning, or even vaporizing the turbid tissue. Furthermore, blood glucose concentration is low compared to many analytes in the human tissue, hence glucose also has very weak Raman signals compared to those of many other analytes, so the signal-to-noise ratio for glucose in tissue measurement is very small. Another drawback is that under laser illumination, human tissues' fluorescence signals are also very strong and tend to mask the already weak Raman signal. The drawbacks make Raman signals directly collected from turbid tissues useless for extracting glucose concentration. One of the Raman prior art references acknowledges the draw backs and attempts to use complicated mathematical methods, such as the so called "fuzzy adaptive resonance theory-mapping", (see U.S. Pat. No. 5,553,616), to extract glucose information from Raman tissue spectra obtained by direct laser illumination. Due to the intrinsic weakness of the signal-to-noise ratio of this type of tissue Raman spectra collection scheme, the method is not feasible for any practical use. Another Raman prior art reference acknowledges this drawback and uses a so called "compound parabolic concentrator", as detailed in U.S. Pat. No. 5,615,673, to enhance the collection efficiency of Raman signals produced from laser irradiation of human tissue. However, this method only increases the collection efficiency of any Raman signals generated from the tissue, and does not necessarily increase the Raman signal of blood glucose fundamentally. Again, due to the intrinsic weakness of the signal-to-noise ratio of this type of tissue Raman spectra collection scheme, the method is not feasible for any practical use.

The state-of-the-art non-invasive methods for measuring glucose non-invasively are not suitable for home and or clinical diabetic blood glucose applications. As a matter of fact, there is no non-invasive device available so far due to the aforementioned major drawbacks. Therefore, there is a need for a new non-invasive technology to overcome the problems associated with measuring blood glucose level in vivo in humans and other animal beings.

SUMMARY OF THE INVENTION

It is therefore an object of the present invention to provide an apparatus for non-invasively measuring blood glucose without drawing blood from a diabetic patient.

It is another object of the present invention to provide a non-invasive blood glucose measuring device that minimizes patient risk and measurement difficulties.

Another object of the present invention is to provide a non-invasive measuring device for home and clinic blood glucose concentration monitoring.

Still another object of the present invention is to provide a portable non-invasive measuring device for blood glucose concentration monitoring.

Yet another object of the present invention is to provide a non-invasive blood glucose measuring device, for use in diabetic glucose level monitoring, that is small, lightweight, immune to temperature variation, and inexpensive to produce.

Briefly, a preferred embodiment of the present invention includes an excitation laser source, a negative pressure based sampling port which interfaces to a human or other animal tissue sample in vivo, a Raman spectrometer, and data analysis and display devices. The device can be made in a compact size and may be portable, and it can be used in homes, offices or clinics.

The excitation laser can operate at any wavelength in the range of 400–1000 nm, but preferably operates in the deep "red" wavelength between 630–670 nm. The excitation wavelength is chosen such that not only the excitation radiation itself, but also the Raman scattering radiation of interest has a relatively lower absorption by the human skin and tissue. Furthermore, the laser is preferably a solid state laser device such as for example, a semiconductor diode laser operating in the aforementioned wavelength range. The laser can be made compact and can be battery operated. The laser radiation can be coupled to the tissue directly by means of optics such as lens, mirrors etc., or via fiber optics.

A negative atmospheric sampling port is made of a vacuum chamber that is connected with an electrically or manually driven vacuum pump which creates a negative air pressure inside the vacuum chamber. Under the negative air pressure, a substantial amount of blood is "sucked" into a small area of the human finger so that measurement of an enhanced Raman signal can be made.

According to the present invention, the Raman spectrometer can either be integrated into a unitary device or be separated via an optical connection, such as a fiber optic cable. As many prior art references have pointed out, the basic elements of the Raman spectrometer include at least a spectrograph, either based on grating or prisms, a charge-coupled device (CCD) optoelectronic detector, a notch filter for blocking the Rayleigh scattering (scattering of the laser wavelength), and data acquisition electronics and software. The detailed art of making a modern compact Raman spectrometer is described in "*Instrumentation for Dispersive Raman Spectroscopy*", by Richard L. McCreery in *Modern Techniques in Raman Spectroscopy* edited by T. Laserna.

Data analysis may be accomplished by a microprocessor and/or be processed by an in-chip algorithm and pre-loaded software. When the preferred embodiment operates as a portable glucose meter, the blood glucose results are displayed in a small flat-panel display unit to allow easy access to the patient carrying the unit.

When the preferred embodiment operates as a home use or clinical use device, blood glucose results can also be sent to a stand-alone or networking computer through one of the standard means of data communication, such as the universal serial bus (USB), RS232, IEEE488, infrared link, or a built-in modem. The data can then be further analyzed and monitored remotely by designated individuals or a health-care institution.

The aforementioned non-invasive human blood glucose measuring device has many applications in blood glucose level monitoring and diagnostics. Further objects and advantages of the subject invention will be apparent from the following detailed description taken in conjunction with the schematic drawings.

IN THE DRAWING

DETAILED DESCRIPTION OF THE PREFERRED EMBODIMENTS

Figure 1:
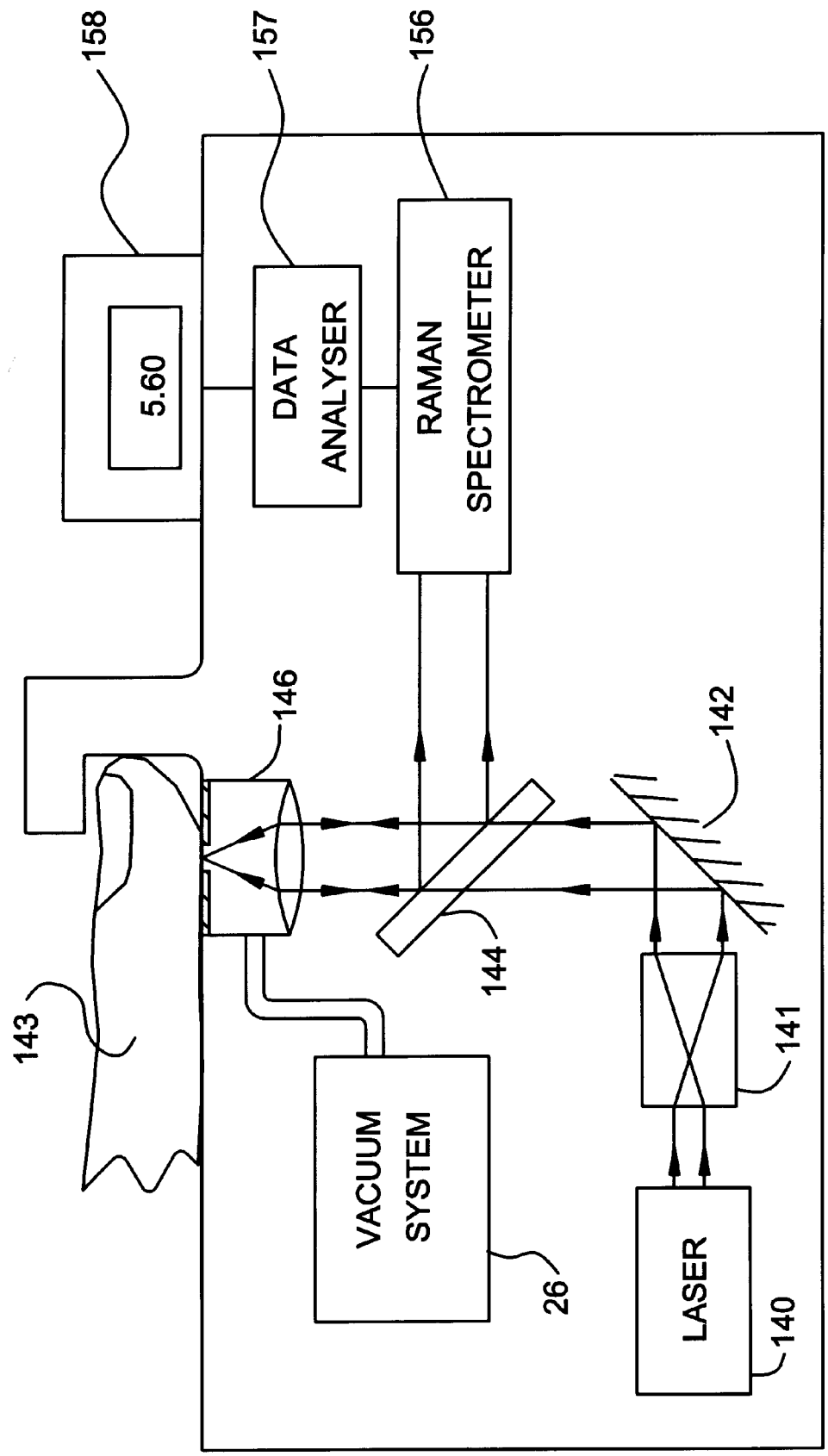
FIG. 1 is a block diagram illustrating a basic configuration of the apparatus used for non-invasive measurement of human blood glucose level in accordance with the present invention, and showing the interrelationship between an exciting laser source, a sampling port, a Raman spectrometer, and data analysis and display devices.

Referring to FIG. 1 of the drawing, which illustrates the interrelationship between an excitation laser source 140, a sampling port 146, a Raman spectrometer 156, and data analysis and display devices 157 and 158, forming a preferred embodiment of the basic apparatus for carrying out the subject invention. The excitation source 140 is a CW laser device emitting low power radiation in a single wavelength, preferably, but not limited to a "red" and NIR wavelength between 630–830 nm, such as for example 632.8 nm from a He-Ne laser device. The exciting wavelength is chosen such that not only is the exciting radiation itself but also the Raman scattering radiation of interest has a relatively lower absorption by the skin and tissue of a human finger 143. For example, by using 632.8 nm as the exciting wavelength, the Raman signatures for glucose and other metabolites will fall into the wavelength range of 635–781 nm (i.e. the wave number range of 50–3000 cm$^{-1}$). This is a range in "deep red" wavelengths, where the absorption by human skin and tissue is substantially lower than in other wavelengths. Also, the fluorescence excited by deep red and NIR wavelengths is substantially lower than that produced by shorter wavelengths. However, the Raman scatter radiation in this range is still detectable by the CCD detector of the spectrometer. Because of this higher penetrating characteristic of the chosen laser wavelength, the power of the excitation laser can be relatively low and typically in the range of a few milliwatts (mW) to a few tens of mW depending on the sensitivity and the efficiency of the Raman spectrometer in use. The laser beam from the excitation source 140 is first passed through a beam expander 141 which increases the diameter of the laser beam and makes it better collimated. The expanded beam is bent 90 degrees toward the sampling port 146 by a mirror 142, or as an alternative, may directly intersect to the sampling port 146.

Still referring to FIG. 1 of the drawing, a beamsplitter 144 is inserted in the path of the laser beam between the mirror 142 and sampling port 146, separating the Raman scattering radiation from the laser radiation and directing it to the Raman spectrometer 156. The beamsplitter can be a dichroic filter that is made so that it is transparent to the laser radiation but reflects the Raman scattering radiation. More preferably, it may be a notch filter which is made so that it reflects the laser radiation and transmits the Raman scattering radiation. It is common to use dichroic beamsplitters or optical notch filters in Raman spectroscopy to block laser radiation, and many prior art references related to Raman spectroscopy have described the use of such components. For example, the use of such components in a typical modern Raman spectrometer system is described by Richard L. McCreery: *"Instrumentation for Dispersive Raman Spectroscopy"*, in *Modern Techniques in Raman Spectroscopy* edited by T. Laserna.

Figure 2:
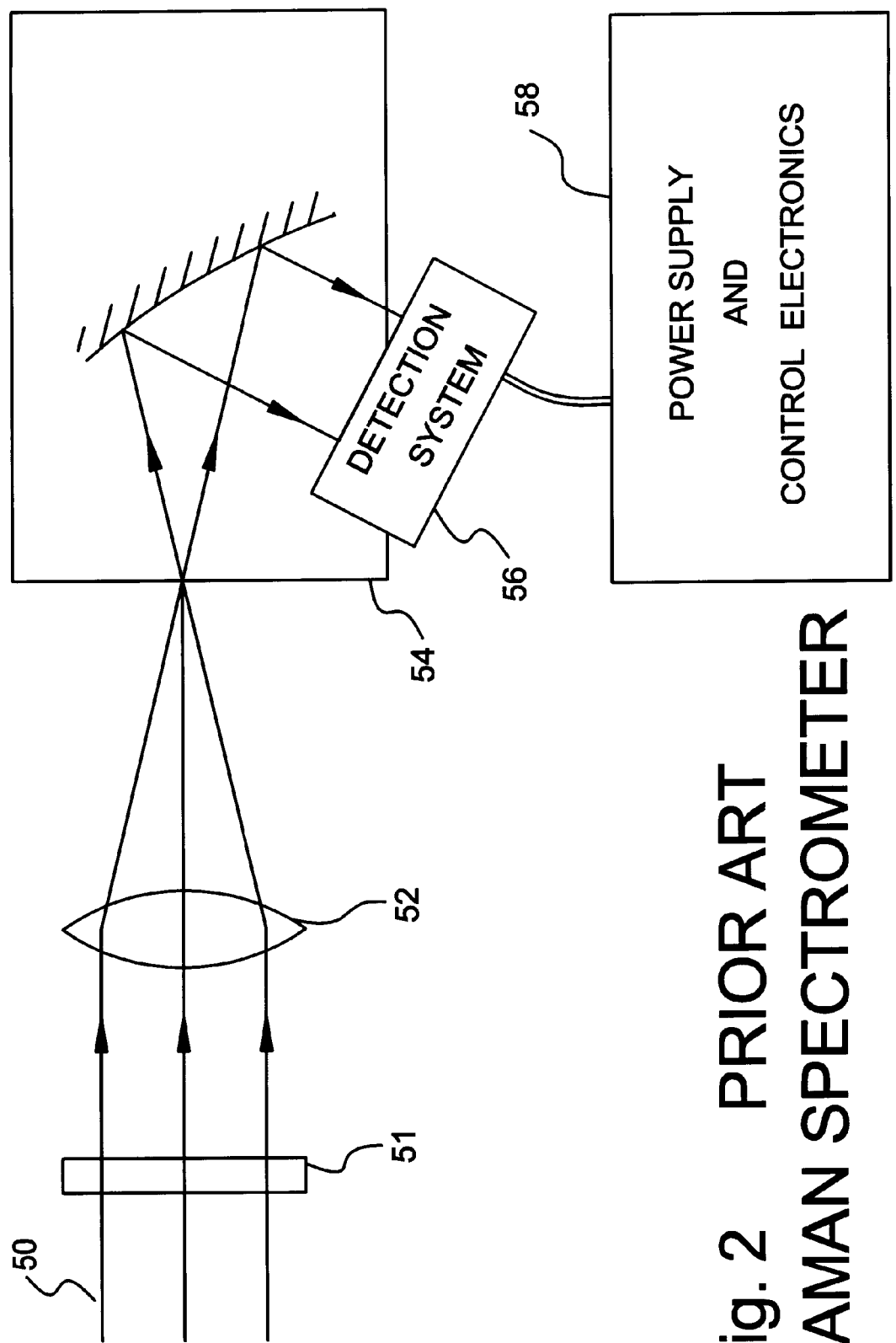
FIG. 2 is a diagram showing a prior art configuration of a Raman spectrometer.

A prior art Raman spectrometer 156, one possible configuration of which is illustrated in FIG. 2, is comprised of a laser radiation rejecting filter 51, a beam condenser lens 52, a spectrograph 54, and a detection system 56. The Raman scattered radiation 50 from the sampling port 146 (FIG. 1) first passes through the rejecting filter 51 which has an optical density of at least 5.0 (transmission of 0.001% of input optical power) to the laser radiation. The lens 52 then condenses the Raman scattered radiation onto the spectrograph with an entrance slit width of 50–200 micron. The spectrograph 54 disperses the radiation by means of one or two dispersing elements (not shown), preferably transmissive holograph gratings, and re-focuses the dispersed radiation onto the detection system 56. Power and control functions for the system are provided by the power supply and control electronics 58. The detection system converts the radiation into electronic digital signals by using a radiation sensitive device, such as a charge coupled device (CCD) or an array of photoelectrical elements, that is cooled to substantially below 0° C., for example, cooled to −40° C. by a thermoelectric cooling unit. Other forms of detection systems can also be used; for example, a group of single detectors which are seated and calibrated in such positions that they sense only the signature peaks of interest from the Raman spectra of the blood glucose and other metabolites.

The digital signals out of the detection system of the Raman spectrometer are sent to the microprocessor of analyzer 157, and processed by an in-chip algorithm and pre-loaded software implementing the chemometric analysis methods such as the partial-least square (PLS) technique.

PLS is a widely used chemometric method used in spectroscopic data analysis. There are many prior art and commercially available software packages for applying PLS to analyze spectroscopic data.

The measured concentration results of glucose or other metabolites are displayed in a small flat-panel display unit 158. The concentration results can also be sent to a stand-alone or networking computer through a standard means of data communication (not shown), such as a universal serial bus (USB), RS232, IEEE488, infrared link, and a built-in modem, for further analysis and monitoring by a designated individual or a health-care institution.

Figure 3:
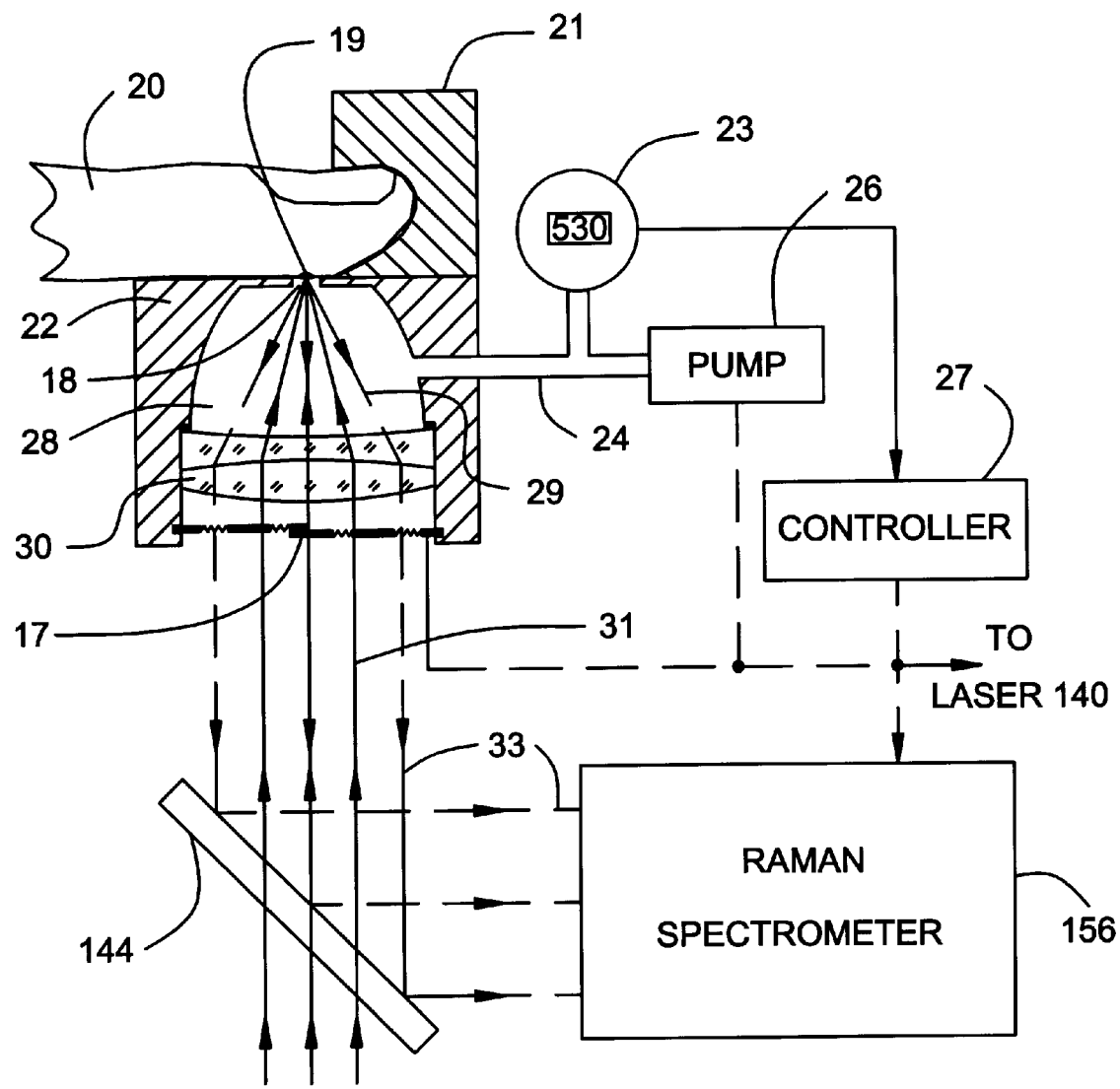
FIG. 3 is a diagram showing a configuration of a sampling port in accordance with the present invention.

Referring to FIG. 3 of the drawing, a exemplary sampling port is shown to include a housing 22 and a focusing and collecting lens 30. The lens should be well corrected for aberrations and preferably include a multi-element based lens, such as a long working distance microscope objective with large numeric aperture for small focal spot and high light collection efficiency. The lens is sealed airtight with the port housing, which forms a vacuum chamber 28 inside the housing when the tested finger 20 is pressed and held over the port opening 18. The opening 18 has a diameter of 2–3 mm and is in the vicinity of the focal point of the lens 30. A mechanically or electrically actuated shutter 17, such as an electromagnetic shutter operated by a touch sensitive switch (not shown), can be attached to the sampling port housing. The shutter is opened only when the finger is pressing on the port opening, so that the laser radiation does not leak out of the device at any time, and is only presented to the opening 18 when the finger is in blocking relationship to the port opening. This is an important safety feature that permits a minor patient to operate the device.

It is a major concern for the Raman spectroscopy based device that the Raman signal from blood be strong enough to be meaningfully measured. In order to increase the signal-to-noise ratio, the prior art tried use the "transparent window" of the human eye (as in the aforementioned U.S. Pat. No. 5,243,983) or tried to increase the signal collecting efficiency (as in the aforementioned U.S. Pat. No. 5,615, 673). However, these methods are either unsafe to the patients or do not fundamentally improve the low signal-to-noise situation. The intensity of the Raman signal depends on not only the exciting laser power but also the amount of blood involved in the Raman scattering process. The present invention uses the vacuum chamber 28 to increase the sample blood concentration at the moment of measurement, and therefore improves the intensity of the Raman signal. The vacuum chamber 28 is then connected to an electrically or manually driven vacuum pump 26 via an air tube 24. When the human finger 20 tightly covers the port opening 18, the vacuum pump 26 is started to create a negative air pressure inside the vacuum chamber 28. A vacuum gauge 23 indicates the vacuum level and stops the vacuum pump 26 when a calibrated value is reached. Under the negative air pressure, a substantial amount of blood is "drawn" into a small area 19 of about the size of the port opening 18. The measurement is then started. The start of the measurement can be triggered either by a manually controlled start key or preferably, by the pressure gauge 23, the gauge being an active device connected to a pressure sensitive controller 27 that, as suggested by the dashed lines 29, actuates either the laser 140, the shutter 17 or spectrometer 156, or any combination thereof when the pressure in chamber 28 reaches some predetermined value. The lens 30 focuses the exciting laser beam 31 onto this small area 19 and collects the Raman scattering radiation 29 coming back from the blood. As discussed before, the laser beam 31 is well collimated, so that it can be effectively focused by the lens 30 onto a relative small area to produce a high concentration, but still substantially below the laser safety level. The laser safety standards can be related to the standard issued by the U.S. Food and Drug Administration (FDA): "FDA Standards for Laser Safety", or "Practical Laser Safety", by D. Winburn. Typically, the laser power density on the tissue should be in the range of a few hundreds mW per centimeter square. The same lens 30 collects the Raman scattering radiation 29 from the excited area and forms an approximately collimated beam of Raman scattering radiation 33. The collimated Raman scattering radiation 33 is then separated from the laser radiation 31 by the beam splitter 144 and redirected to the Raman spectrometer 156 for further processing.

Determining the concentration of the blood glucose and other metabolites from the signature Raman spectra produced by the Raman spectrometer 156 involves two major aspects: background signal removal and calibration.

The background signal comprises the fluorescent and other scattering radiation from skin, fat, tissues and components other than blood, which in general shows up as a broad-band smooth spectrum superposed by the Raman signature spectrum in the wavelength range of interest. This background signal can be removed from the measured Raman spectrum by using a variety of analytical methods, such as curve fitting and subtraction. These methods have been widely used in the prior art to obtain useful Raman spectra from Raman signals with strong background signals. One example of such methods is discussed by T. Iwata, et al in *Applied Spectroscopy*, vol 48, 1453 (1994).

Furthermore, this type of background signal can be removed from the measured Raman spectrum by another technique forming a part of this invention: i.e., numerically subtracting a pre-measured background spectrum. Such background spectrum can be obtained by reversing the vacuum pump 26 to produce a positive air pressure inside the vacuum chamber 28 when the human finger 20 is tightly covering the port opening 18. Under the positive air pressure, the blood is "driven" away from the measured area on the finger. The spectrum taken at this moment contains no significant Raman signature peaks from the blood, and can thus serve as the background spectrum.

A calibration process is to generate the correlation between the measured concentration and the actual or best-believed concentration. To generate an accurate correlation in the calibration, both the measured concentration and the actual or best-believed concentration are obtained collaterally. The actual or best-believed concentration can be measured by any prior art invasive method, such as, for example, using chemical reaction based devices in the clinical lab. The measured concentration is then determined by numerically calculating the sum of the intensity of the Raman signature spectra over the wavelength range of interest. There are at least two factors that will affect the value of the measured concentration: the measured spot size on the finger and the amount of blood involved in the measurement. To assure a repeatable measured spot size in the calibration as well as in the normal measurement, a finger locator 21, as illustrated in FIG. 3, one of the preferable designs, is used to hold the finger in nearly the same position every time a measurement is made. The amount of blood drawn into the measured area depends on the strength of the negative air pressure inside the vacuum chamber 28, and the physiological properties of the patient's finger. As pointed out above, the vacuum gauge 23 is used to monitor this air pressure and trigger the spectrum measurement. When doing calibration, the strength of the negative air pressure inside the vacuum chamber 28 is changed until a reasonably strong Raman scattering signal is reached. Then the vacuum gauge reading is recorded and the measured concentrations of the blood glucose and other metabolites are calculated from the Raman scattering signal. As a reference value, the actual or best-believed concentration is also obtained by the means discussed above. Once the correlation relationship between the measured concentration and the actual or best-believed concentration is established, the corresponding vacuum gauge reading is defined as the calibration value and is used for triggering every Raman signal measurement until the next calibration is carried out.

The aforementioned calibration method can be designed into the device as an algorithm which is controlled by, as also mentioned above, a microprocessor, or a in-chip algorithm. It is preferable to calibrate the device to individual patients due to the possible physiological and optical differences of the living being; for example, the difference of those properties related to human skin tissues. It is also preferable to calibrate the device to the individual patient at an experimentally determined frequency, i.e., the time intervals between two calibrations. The calibration can be done either by the individual patient himself/herself, or by a service person. The calibration can be done against a standard (a golden device) or a reference sample (in vitro).

Figure 4:
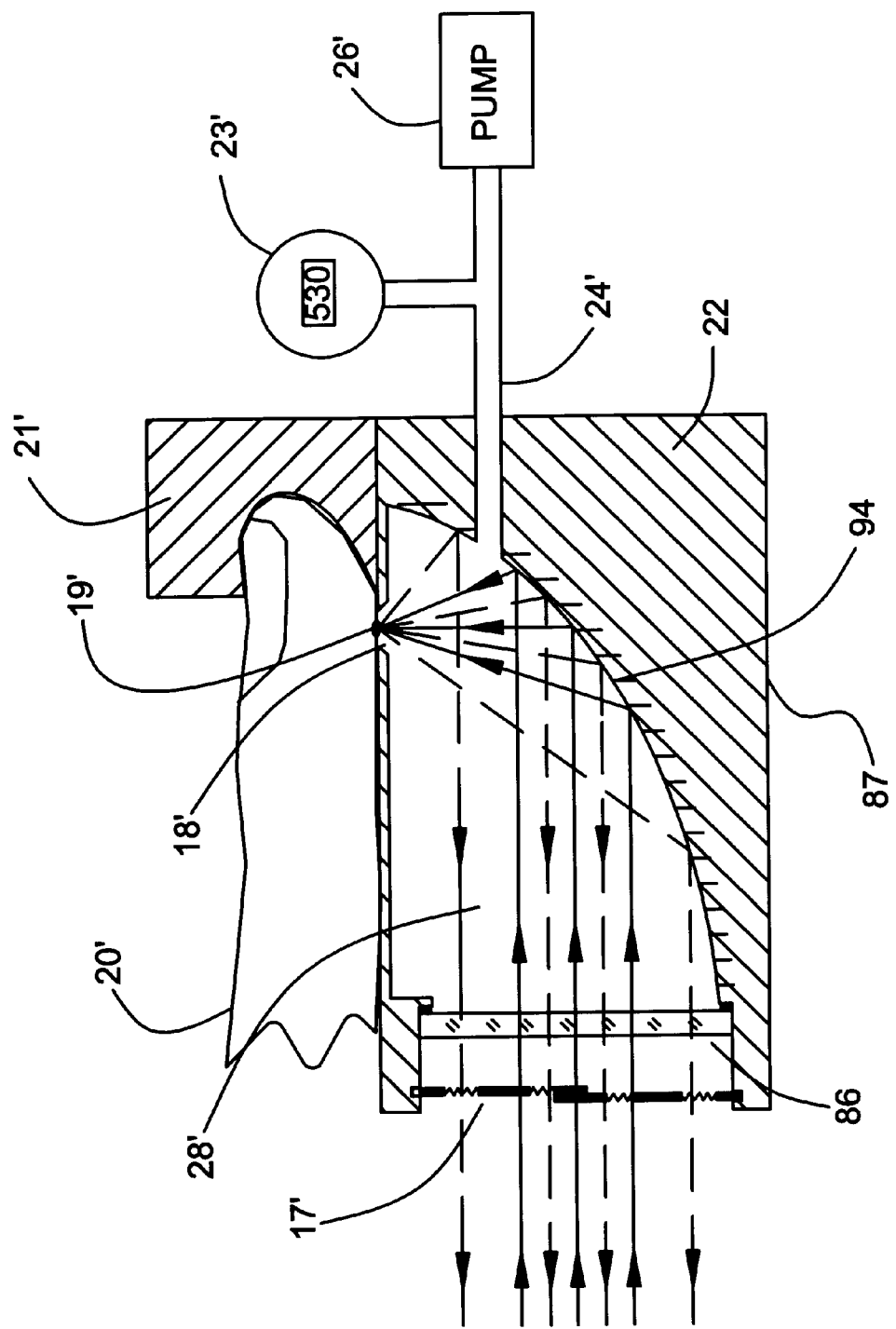
FIG. 4 is an alternative embodiment of a sampling port in accordance with the present invention.

FIG. 4 shows an alternative embodiment of the sampling port structure. The components are otherwise similar to those of FIG. 3 except that an off-axis parabolic mirror 94 and an optical window 86 are used to replace the focusing/collecting lens 30 of the FIG. 3 embodiment. The optical window 86 is used to seal one side of the housing 87 to form a vacuum chamber 28'. And again, the port opening 18' is in the position of the focal point of the mirror 94. The surface of the mirror 94 is preferably parabolic shaped, but it can be of any other suitable shape that produces the desired collimating/focusing function. For example, it can be a concave mirror. Mirror 94 is polished and preferably coated with a highly reflective coating material to enhance the reflectance of light in the aforementioned wavelength range. Note that this alternative embodiment has the advantage of having less chromatic aberration generated from the off-axis parabolic mirror 94 as compared to that of the focusing lens 30 (FIG. 3).

Figure 5:
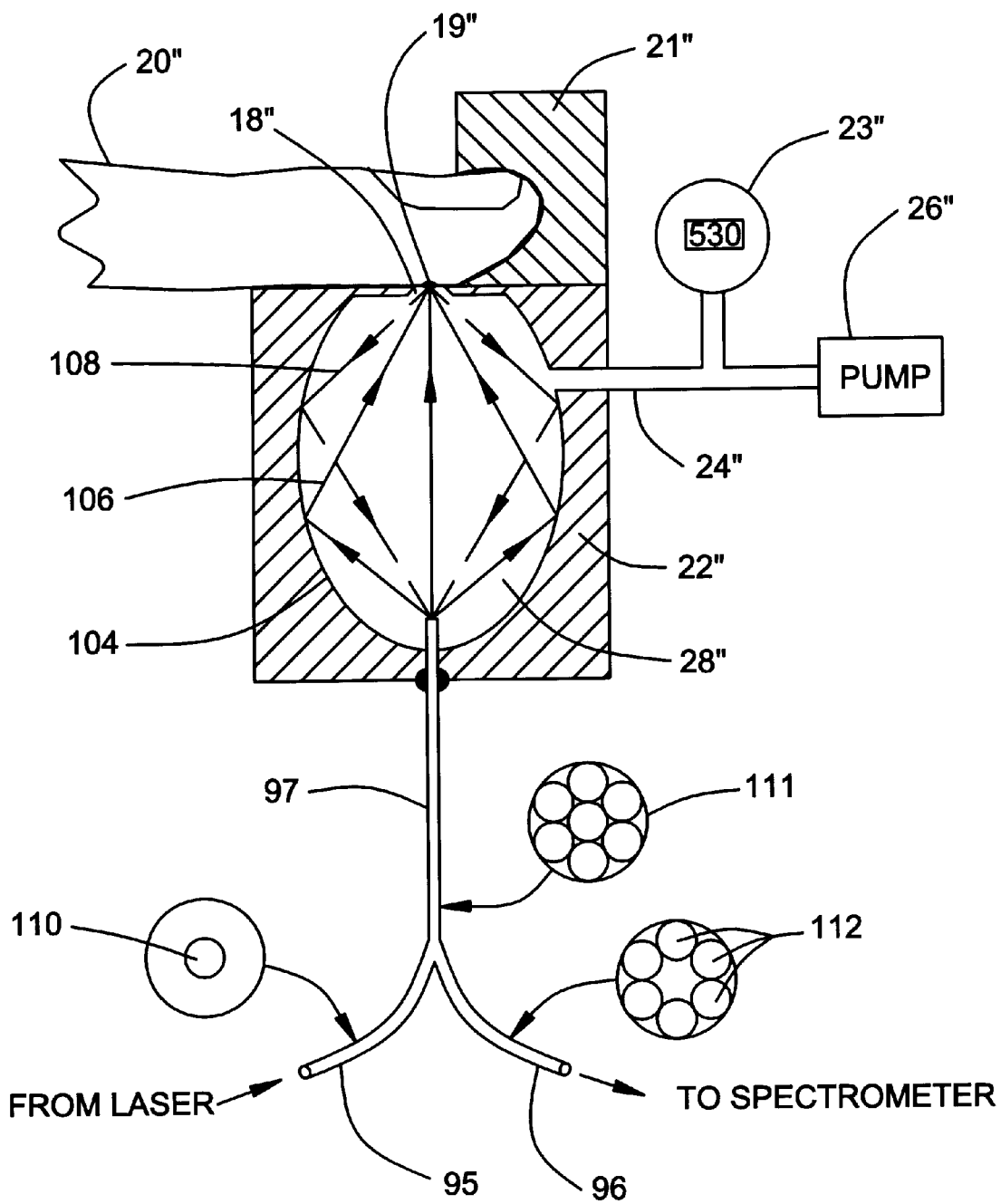
FIG. 5 is yet another alternative embodiment of a sampling port in accordance with the present invention.

FIG. 5 shows another alternative embodiment of the sampling port structure. Here, an n-around-one fiber bundle 97 is sealingly engaged to and extends into the vacuum chamber 28''. The internal surface 104 of the chamber is preferably ellipsoidally shaped, with the fiber bundle tip 99 positioned at one of the focal points and the port opening 18'' on the other. Again, this surface 104 is polished and preferably coated with a highly reflective coating material to enhance the reflectance of light within the aforementioned wavelength range. The fiber bundle 97 has two branches, 95 and 96, on the other end. The branch 95 contains the center fiber 110 for introducing the laser radiation into the sampling port, while the branch 96 contains the surrounding fibers 112. The center fiber 110 has a relatively larger numerical aperture (N.A.), and the output laser radiation 106 is spread across a larger solid angle, so that the laser radiation 106 can be re-focused onto the port opening 18'' by the ellipsoidally shaped surface 104. The Raman scattering radiation 108 returning from the finger is collected by the surface 104 and refocused onto the surrounding fibers of the n-around-one fiber bundle whereby it is directed to the Raman spectrometer 156 through the branch 96. Note that this alternative embodiment has the advantage of having higher Raman scattering radiation collectivity. However, it requires that the fiber have a much larger N.A. to make use of this advantage.

Although the present invention has been described in terms of specific embodiments that are related to measurements on a human finger, it is anticipated that the same measurements can be carried out on other parts or portions of a human or other animal subject, such as earlobe, arm, palm, et al. It is to be noted that the several references identified herein are expressly incorporated into and form a part of this disclosure.

Although the present invention has been described in terms of specific embodiments it is anticipated that alterations and modifications thereof will no doubt become apparent to those skilled in the art. It is therefore intended that the following claims be interpreted as covering all such alterations and modifications as fall within the true spirit and scope of the invention.

We claim:

1. A non-invasive blood inspection apparatus comprising:
   means forming a chamber having an opening that is small compared to the size of a particular human/animal body part;
   pumping means for reducing the fluid pressure within said chamber when said opening is blocked by a portion of the human/animal tissue forming the body part, the reduced pressure providing concentration of the blood within the portion of tissue blockingly engaging said opening;
   means for projecting luminous energy through said chamber and onto said portion of said tissue and for collecting luminous energy reflected from the tissue;
   shuttering means for selectively blocking said luminous energy when said opening is not engaged by said tissue;
   pressure sensing means responsive to the pressure in said chamber and operative to close said shuttering means when the pressure within said chamber is above a predetermined level so as to prevent said luminous energy from passing through said opening unless said opening is blocked by said tissue; and
   means for analyzing the collected luminous energy to determine a certain characteristic of the blood concentrated in said tissue.

2. A non-invasive blood inspection apparatus comprising optical non-invasive blood inspection apparatus as recited in claim 1 wherein said means for projecting luminous energy includes means for focusing the projected luminous energy onto said portion of tissue and for collecting and substantially collimating the collected luminous energy reflected from said tissue.

3. A non-invasive blood inspection apparatus as recited in claim 2 wherein said means for projecting includes a beam splitter means for separating particular wavelengths from said collected luminous energy and for reflecting the particular wavelengths into said means for analyzing.

4. A non-invasive blood inspection apparatus as recited in claim 3 wherein said means for analyzing comprises a Raman spectrometer.

5. A non-invasive blood inspection apparatus as recited in claim 4 wherein said means for projecting includes a laser light source.

6. A non-invasive blood inspection apparatus as recited in claim 1 wherein said means for projecting includes a laser light source.

7. A non-invasive blood inspection apparatus as recited in claim 1 wherein the means forming the chamber includes a reflective interior wall that is oriented to receive said luminous energy and is shaped such that luminous energy reflected therefrom is focused onto a spot within said opening.

8. A method of non-invasively analyzing the blood of a living human/animal comprising the steps of:
   providing a chamber having an opening that is small compared to the size of a particular human/animal body part;
   positioning said particular body part of a human/animal patient in engagement with said opening;
   reducing the fluid pressure within said chamber when said opening is blocked by the portion of human/animal tissue forming the body part, the reduced pressure providing concentration of the blood within the portion of tissue blockingly engaging said opening;

projecting luminous energy through said chamber and onto said portion of tissue;

providing a shutter for selectively preventing said luminous energy from entering said chamber;

monitoring the pressure within said chamber and causing said shutter to open only in the event that the pressure falls below a predetermined level;

collecting luminous energy reflected from said portion of tissue; and analyzing the collected luminous energy to determine certain characteristics of the blood concentrated in said tissue.

9. A method as recited in claim 8 wherein the step of collecting includes collecting only luminous energy that is limited to a predetermined range of wavelengths.

10. A method as recited in claim 8 wherein the step of projecting said luminous energy includes focusing the luminous energy onto a spot of said portion of said tissue that is substantially smaller than the area of said opening.

11. A method as recited in claim 8, wherein said certain characteristics include the blood glucose level of the patient.

12. A method as recited in claim 8, wherein the step of analyzing includes using a Raman spectrometer to analyze said collected luminous energy.

13. A method as recited in claim 8, wherein the step of collecting includes using a beam splitter to separate a particular wavelength from said collected luminous energy and to reflect the particular wavelength for analyzing purposes.

14. A method as recited in claim 13, wherein the step of analyzing includes using a Raman spectrometer to analyze the collected luminous energy.

15. A non-invasive blood inspection apparatus comprising:

means forming a chamber having an opening that is small compared to the size of a particular human/animal body part, said chamber including a reflective interior wall having a curved surface;

pumping means for reducing the fluid pressure within said chamber when said opening is blocked by a portion of the human/animal tissue forming the body part, the reduced pressure providing concentration of the blood within the portion of tissue blockingly engaging said opening;

means for projecting luminous energy into said chamber and onto said portion of said tissue, said reflective interior wall of said chamber being oriented to reflect and focus said luminous energy onto a spot within said opening;

means for collecting luminous energy reflected from the tissue via said reflective interior wall;

means for analyzing the collected luminous energy to determine a certain characteristic of the blood concentrated in said tissue.

16. A non-invasive blood inspection apparatus as recited in claim 15, wherein said means for analyzing comprises a Raman spectrometer.

17. A non-invasive blood inspection apparatus as recited in claim 15, wherein:

said means for projecting luminous energy into said chamber includes a center fiber; and said means for collecting luminous energy includes a plurality of surrounding fibers surrounding said center fiber.

18. A non-invasive blood inspection apparatus as recited in claim 17 wherein said center fiber has a numeric aperture that is substantially larger than the numeric aperture of each of said surrounding fibers.

19. A non-invasive blood inspection apparatus as recited in claim 15, wherein said reflective interior wall of said chamber is ellipsoidally shaped.

20. A non-invasive blood inspection apparatus as recited in claim 15, wherein said means for projecting luminous energy provides projection of Raman scattering radiation, whereby said reflective interior wall of said chamber provides for high Raman scattering radiation collectivity.

* * * * *